(12) United States Patent
Forsell (10) Patent No.: US 7,499,753 B2
(45) Date of Patent: Mar. 3, 2009

(54) URINARY DYSFUNCTION TREATMENT APPARATUS

(75) Inventor: Peter Forsell, Zug (CH)

(73) Assignee: Urologica AG, Baar (CH)

( * ) Notice: Subject to any disclaimer, the term of this patent is extended or adjusted under 35 U.S.C. 154(b) by 552 days.

(21) Appl. No.: 10/703,444

(22) Filed: Nov. 10, 2003

(65) Prior Publication Data

US 2004/0172087 A1    Sep. 2, 2004

Related U.S. Application Data

(63) Continuation-in-part of application No. 09/893,509, filed on Jun. 29, 2001, now abandoned.

(30) Foreign Application Priority Data

Jun. 28, 2001    (SE) .................................. 0102312

(51) Int. Cl.
*A61N 1/18*    (2006.01)
(52) U.S. Cl. ........................................ 607/41; 607/40
(58) Field of Classification Search .............. 607/40–41
See application file for complete search history.

(56) References Cited

U.S. PATENT DOCUMENTS 5,919,220 A    7/1999    Stieglitz et al.
6,061,596 A    5/2000    Richmond et al.
6,415,186 B1    7/2002    Chim et al.
2002/0062060 A1    5/2002    Gross et al.
2003/0004553 A1*    1/2003    Grill et al. .................... 607/40

FOREIGN PATENT DOCUMENTS

WO    WO 00/19939         4/2000
WO    WO 01/10357 A1      2/2001
WO    WO 01/12108 A1      2/2001

OTHER PUBLICATIONS

"Sphincter stimulators to prevent incontinence" from Nursing Times, Nov. 15, 1973.

* cited by examiner

*Primary Examiner*—Carl H Layno
*Assistant Examiner*—Deborah Malamud
(74) *Attorney, Agent, or Firm*—Nixon & Vanderhye P.C.

(57) ABSTRACT

An apparatus for treating urinary incontinence comprises an electrically powered stimulation device that electrically stimulates the urethral sphincter of a urinary incontinent patient and a hand-held wireless remote control that controls the stimulation device. A stress or urge incontinent patient operates the remote control to: i) switch off the electrically powered stimulation device, when the patient wants to urinate, and switch on the electrically powered stimulation device, when the patient has finished urinating; and ii) control the stimulation device as needed at any time over the course of a day to promptly adjust the intensity of the electric stimulation of the urethral sphincter to quickly increase the tonus of the urethral sphincter.

84 Claims, 4 Drawing Sheets

URINARY DYSFUNCTION TREATMENT APPARATUS

This application is a continuation-in-part of application Ser. No. 09/893,509, filed Jun. 29, 2001, now abandoned, the disclosure of which is hereby incorporated by reference herein.

FIELD OF THE INVENTION

The present invention relates to apparatuses and methods for treating urinary incontinence.

Urinary incontinence may involve the inability to control the muscle that contracts the urine bladder. This condition is called overflow incontinence. In particular, partially paralysed patients may suffer from this condition. On the other hand, urinary incontinence may involve the inability to keep the urethral sphincter completely closed, a condition called urinary stress incontinence. In a urinary stress incontinent patient the urethral sphincter is unable to prevent urine from being expelled from the bladder during transient increases in intra-abdominal pressure, which can be caused by sneezing, coughing or laughing, or by lifting heavy goods. Moreover, urinary incontinence may involve spontaneous activity of the bladder causing a compelling feeling of the patient that the bladder needs to be emptied, although the bladder maybe contains little urine. This condition is called urinary urge incontinence.

Urinary stress and urge incontinences are widespread diseases. Although some people suffering from these diseases are helped through training of the muscles in the pelvic floor, too many have severe problems with urine leakage. Many different implant devices have been tried to remedy this kind of urinary incontinence. For example, there is a prior manually operated urinary incontinence treatment apparatus having an artificial hydraulic sphincter device engaging the urethra and connected to an elastic reservoir implanted in the scrotum or in the region of the labia majora. A disadvantage of this prior apparatus is that over time a hard fibrosis is developed around the reservoir, which may cause a malfunction of the pumping components. Furthermore, it is a rather complicated task to manually squeeze the elastic implanted reservoir to pump hydraulic fluid to open the sphincter device when the patient needs to urinate. In particular, women can get their fingers wet. The created fibrosis will sooner or later become a hard fibrotic layer, which may make it even more difficult to pump the reservoir. Yet a further disadvantage is that the use of hydraulic fluid always entails a risk of fluid leaking from implanted hydraulic components.

A prior hydraulic apparatus designed to compress the urethra is disclosed in U.S. Pat. No. 5,520,606. A prosthetic sphincter with an inflatable cuff, which surrounds the urethra or encloses it on two sides, is disclosed in, for example, U.S. Pat. Nos. 4,571,749 and 4,222,377. U.S. Pat. No. 4,969,474 discloses a hydraulic method for treating both men and women having urinary stress incontinence in the same way. The apparatus of U.S. Pat. No. 4,969,474 includes a reservoir containing fluid and an inflatable compression means designed to compress the urethra without risking tissue loss or causing necrosis to occur. An artificial hydraulically operated urethral sphincter employing an external magnet to achieve closure of the urethral cuff is disclosed in U.S. Pat. No. 5,562,598.

A prior mechanical prosthetic sphincter disclosed in U.S. Pat. No. 4,619,245 comprises a manually controllable actuating component which is implanted at a convenient location in the patient's body.

U.S. Pat. No. 4,739,764 discloses a method for treating urinary incontinence by electric stimulation of an inferior somatic nerve connected to the urethral sphincter. The function of the urethral sphincter is affected by applying electric pulse trains to the somatic nerve.

U.S. Pat. No. 6,061,596 discloses a system for regularly conditioning and training the pelvic muscles of a urinary stress or urge incontinent patient with electric stimulation so as to restore voluntary control to the patient. The pelvic muscles are stimulated, i.e., conditioned, for 15-60 minutes each day using intermittent trains of electrical pulses. Accordingly, during the rest of each day, i.e. at least 23 hours, the pelvic muscles are not stimulated. The system includes a control unit and an external transmitting coil that may be contained within a cushion on which the patient sits during training. The transmitting coil is inductively coupled to receiving coils contained in implanted microstimulators to induce a voltage in the receiving coils by which power and data are transmitted to the microstimulators. The patient can switch the system on and off using an external interface.

U.S. Pat. Appl. Publication No. 2002/0062060 A1 discloses a urinary stress or urge incontinence treatment device, which is sensor controlled and is normally not in operation unless signals from the sensors indicate a condition that is likely to cause involuntary urine flow. The sensors generate signals responsive to motion or to intravesical or abdominal pressure, or to urine volume in the bladder. The signals from the sensors are indicative of possible incontinence that may occur due to coughing, laughing, or other strain or motion of abdominal muscles. The patient can switch the device on and off using a magnet.

SUMMARY OF THE INVENTION

An object of the present invention is to provide new convenient urinary incontinence treatment apparatuses, the performance of which may be controlled by the patient at any time after operation, particularly when various needs arise over the course of a day, so that the patient is substantially always satisfied or comfortable.

Another object of the present invention is to provide urinary incontinence treatment methods that enable the patient to control the treatment at any time after operation, particularly when various needs arise over the course of a day, so that the patient is substantially always satisfied or comfortable.

Accordingly, in accordance with a first aspect of the present invention, there is provided an apparatus for treating urinary incontinence, comprising an electrically powered stimulation device implantable in a urinary incontinent patient and adapted to electrically stimulate the urethral sphincter all the time, except when the patient wants to urinate, to maintain a sufficient tonus of the urethral sphincter that prevents urine from passing past the urethral sphincter, and a control device that controls the stimulation device, the control device including a hand-held wireless remote control adapted to control the stimulation device from outside the patient's body, wherein the wireless remote control is operable by the patient to:

i) switch off the electrically powered stimulation device, when the patient wants to urinate, and switch on the electrically powered stimulation device, when the patient has finished urinating; and ii) control the stimulation device as needed at any time over the course of a day to promptly adjust the intensity of the electric stimulation of the urethral sphincter, so that the tonus of the urethral sphincter is quickly increased, whereby the patient is able to maintain continence.

Preferably, the patient operates the wireless remote control to control the stimulation device to temporarily increase the intensity of the electric stimulation of the urethral sphincter, so that the tonus of the urethral sphincter is increased, when the patient expects an abrupt increase in the abdominal pressure. Coughing, sneezing, laughing or the like can cause such an abrupt increase in the abdominal pressure. The wireless remote control is suitably operable by the patient to control the stimulation device to adjust the intensity of the electric stimulation of the urethral sphincter to one of a plurality of different preselected intensity levels. For example, the remote control may be provided with a "cough-button" that controls an electric stimulation intensity level high enough to prevent urine leakage when the patient coughs, and be provided with a "laugh-button" that controls another electric stimulation intensity level high enough to prevent urine leakage when the patient laughs. In this manner, the remote control may be provided with several buttons that control different electric stimulation intensity levels required to prevent urine leakage during different situations that the patient may face. By using different pre-selected intensity levels to maintain continence during different situations, the urethral sphincter is not subjected to unnecessary high stimulation intensity levels that may be harmful to the urethral sphincter in the long run.

Thus, a urinary stress or urge incontinent patient using the apparatus of the present invention has full control over his or her bladder function, since he or she is able to keep the urethral sphincter completely closed at any time by means of the stimulation device by conveniently using the hand-held wireless remote control whenever he or she likes during the day. For example, the patient may increase the stimulation intensity in advance, when the patient is about to laugh or lift heavy goods, or feels that he or she is about to sneeze or cough. On the other hand, the patient can control the stimulation device to cease supplying the stimulation device with electric energy when the patient wants to urinate.

The ability of the patient to control the stimulation in advance when he or she is faced with a situation where incontinence may occur, should not be underestimated. A feedback control system based on, for example, a pressure sensor in the abdomen, as suggested by prior art, would not react fast enough, for example when the patient already is sneezing. Thus, leakage of urine would occur before such a feedback control system has responded to a measured increased pressure in the patient's abdomen and controlled the stimulation device to start the stimulation of the urethral sphincter. Also, there is some delay before the urethral sphincter muscle reacts to the electric stimulation. In contrast, the patient controlled apparatus of the present invention allows the patient to operate the hand-held wireless remote control well in advance, for example by pressing a special "sneeze button" on the remote control, when the patient feels a need for sneezing or the like. The amount of stimulation in such a situation may be previously tested and pre-programmed. As a result, a urinary incontinent patient using the apparatus of the present invention would experience a huge increase in the quality of life.

The control device of the present invention may control the stimulation device to cyclically alternate between an operation mode, in which the urethral sphincter is stimulated, for example with energy pulses, and a rest mode, in which the urethral sphincter is not stimulated. As a result, the urethral sphincter muscle is able to "recover" during the rest modes, so that it responds to the stimulation over the long run. Of course, the durations of the rest modes should be short enough so that the tonus of the urethra sphincter muscle does not decrease too much during each rest mode.

In a preferred embodiment of the present invention, the apparatus comprises a source of energy, preferably an electric source of energy controllable by the control device to supply electric energy for operating the stimulation device. The control device is adapted to continuously or cyclically supply the stimulation device with electric energy from the electric source of energy to keep the urethral sphincter closed, except when the patient wants to urinate. As a result, the apparatus of the present invention provides a simple and effective control of the energy supplied to implanted components of the apparatus, which ensures an extended and reliable functionality of the apparatus, possibly for the rest of the patient's life and at least many years.

In accordance with a second aspect of the present invention, there is provided an apparatus for treating urinary overflow incontinence, comprising an electrically powered stimulation device implantable in a urinary overflow incontinent patient and adapted to electrically stimulate the urine bladder contraction muscle to contract the bladder, and a control device that controls the stimulation device, the control device including a hand-held wireless remote control adapted to control the stimulation device from outside the patient's body, wherein the wireless remote control is operable by the patient to:

i) switch on the electrically powered stimulation device to cause the urine bladder contraction muscle to contract the bladder, when the patient wants to urinate, and switch off the electrically powered stimulation device, when the patient has finished urinating; and ii) control the stimulation device to adjust the intensity of the electric stimulation of the urine bladder contraction muscle to empty the bladder in a manner that is comfortable to the patient.

When the bladder muscle is stimulated, it is important that the stimulation intensity is optimal, so that on one hand the bladder is not contracted too forcefully and on the other hand is not contracted too weakly. Too forceful a contraction of the bladder would be painful to the patient and too weak a contraction would result in a long urination time and possibly an insufficiently emptied bladder. The present invention allows the patient to adjust the stimulation intensity so that the urination is neither painful nor takes a time longer than that of a continent person, i.e., the patient's bladder is emptied in a manner that is comfortable to the patient.

A urinary overflow incontinent patient might also have problems with urine bladder leakage. Therefore, the apparatus may suitably include an electrically powered additional stimulation device adapted to directly engage with and electrically stimulate the urethral sphincter to increase the tonus thereof to counteract the leakage of urine from the bladder. Conveniently the hand-held wireless remote control also controls the additional stimulation device and is operable by the patient to switch off the additional stimulation device, when the patient wants to urinate, and switch on the additional stimulation device, when the patient has finished urinating. Preferably, the wireless remote control is operable by the patient to control the additional stimulation device to adjust the intensity of the electric stimulation of the urethral sphincter so that urine leakage from the bladder is satisfactorily counteracted.

The advantage with the urinary overflow incontinent treatment apparatus is huge. For example, paraplegic patients today are subjected to an inconvenient procedure in which a catheter is used to regularly empty the urinary bladder. This procedure often gives rise to bacteria contamination and intermittent infection problems of the urinary tract. In contrast, the paraplegic patient can conveniently use the hand-held wireless remote control to electrically stimulate the urine contraction muscle to empty the bladder, and, thereby avoid infection problems. To further increase the convenience of the paraplegic patient, the apparatus may be provided with a feed back control system warning the patient when it is time to urinate due to an almost full urine bladder.

In a preferred embodiment of the present invention, the urinary overflow incontinence treatment apparatus comprises a source of energy, preferably an electric source of energy controllable by the control device to supply electric energy for operating the stimulation device. The wireless remote control is operable by the patient to control the electric source of energy to momentarily supply the stimulation device with electric energy to cause the urine bladder contraction muscle to momentarily contract the bladder when the patient wants to urinate.

The embodiments of the invention that are described below are applicable to the urinary incontinence treatment apparatus according to the first aspect of the present invention, as well as the urinary overflow incontinence treatment apparatus according to the second aspect of the present invention.

An important problem associated with electric stimulation of muscle tissues is that the applied voltage intensity that provides the desired stimulation of the urethral sphincter or urine bladder contraction muscle might be reduced over time, due to increasing electric resistance caused by the formation of fibrosis where the electrodes engage the muscle. This problem is solved by a preferred embodiment of the present invention, in which the electric source of energy provides a current through the electrodes and the control device is adapted to control the electric source of energy to release electric energy such that the intensity of the current flowing through the electrodes is equal to a predetermined value. As a result, decreasing current intensity caused by the formation of fibrosis where the electrodes engage the muscle can be compensated for. Thus, if the current through the electrodes decreases the control device automatically controls the electric source of energy to release more electric energy to restore the desired current flow.

Advantageously, the control device is adapted to control the electric source of energy to release energy in the form of an alternating current. The inventor has found that, unlike an alternating current, a direct current may cause electrolysis in the muscle. Such electrolysis may injure the muscle.

As a complement to the patient controlled embodiments of the present invention, at least one implantable sensor for sensing at least one physical parameter of the patient may be provided for sending to the control device signals based on the sensed physical parameter. Thus, the apparatus according to the first aspect of the present invention may include a sensor adapted to sense as the physical parameter the pressure against the urethral sphincter exerted by the urine bladder, and the control device may automatically control the electric stimulation device to increase the stimulation of the urethral sphincter in response to the sensor sensing an abrupt increase in pressure caused by bladder contraction or increased abdominal pressure when the patient coughs or the like, to avoid incontinence. Alternatively, the sensor may be adapted to sense as the physical parameter the patient's orientation, and the control device may control the electric stimulation device to decrease the stimulation intensity on the urethral sphincter in response to the orientation sensor sensing that the patient is lying down.

The urinary overflow incontinence treatment apparatus according to the second aspect of the present invention may include a pressure sensor for directly or indirectly sensing the pressure in the urine bladder. The expression "indirectly sensing the pressure in the urine bladder" should be understood to encompass cases where the sensor senses the pressure exerted by the bladder against the stimulation device or human tissue of the patient. Alternatively, or in combination, the apparatus may include a volume sensor that senses the volume of the urine in the bladder. Such a volume sensor may be designed to indirectly sense the volume, for example a strain sensor applied on the bladder wall or a motion sensor attached on the bladder and adapted to sense increasing movements of the bladder with increasing urine volume. The control device may conveniently initiate an alarm signal for the attention of the patient in response to the pressure sensor sensing a pressure exceeding a predetermined value, or in response to the volume sensor sensing a volume exceeding a predetermined value.

The control device may include at least one external signal transmitter or transceiver and at least one internal signal receiver or transceiver implantable in the patient.

The control device may include an internal control unit to be implanted in the patient. The internal control unit may suitably directly control the stimulation device in response to signals from the sensor. In response to signals from the sensor, the internal control unit may send information thereon to outside the patient's body. The internal control unit may also automatically control the stimulation device in response to signals from the sensor. For example, for a stress or urge incontinent patient, depending on the different needs of the individual patients, the internal control unit may control the stimulation device, either to efficiently stimulate the urethral sphincter, so that the urethral sphincter for certain is completely closed in response to an abrupt increase in pressure in the urine in the bladder, or to reduce the stimulation, in response to the sensor sensing that the patient is lying down.

The control device may also, or alternatively, comprise an external control unit outside the patient's body, preferably incorporated in the hand-held wireless remote control. The external control unit may, suitably directly, control the stimulation device in response to signals from the sensor. The external control unit may store information on the physical parameter sensed by the sensor and may be manually operated to control the stimulation device based on the stored information. In addition, there may be at least one implantable sender for sending information on the physical parameter sensed by the sensor.

Where the control device comprises an internal control unit, preferably including a microprocessor, and an external control unit outside the patient's body, the internal control unit may be programmable by the external control unit, for example for controlling the stimulation device over time. Alternatively, the internal control unit may control the stimulation device over time in accordance with an activity schedule program, which may be adapted to the patient's needs.

Conveniently, the external control unit may load the internal control unit with data in accordance with a loading mode only authorised for a doctor. For specialised controls of the stimulation device, such as electric power, electric pulse frequency etc. the external control unit may control the internal control unit in accordance with a doctor mode only authorised for the doctor. For simple controls of the stimulation device, such as on and off, and change in stimulation intensity, the external control unit may control the internal control unit in accordance with a patient mode permitted for the patient. Thus, by using the external control unit in accordance with different modes, it is possible to have certain functions of the stimulation device controlled by the patient and other more advanced functions controlled by the doctor, which enables a flexible post-operation treatment of the patient.

The control device may be adapted to control the source of energy to intermittently release energy in the form of a train of pulses, for direct use in connection with the power of the stimulation device. Where the source of energy comprises an electric source of energy an implantable capacitor is suitably provided to produce the train of electric pulses from the released electrical energy. In this case the term "direct" is used to mean, on one hand, that the released electrical energy is used while it is being released by the control device, and on the other hand, that the released electrical energy may be somewhat delayed, in the order of seconds, by for instance an electric energy stabiliser before being used in connection with the power of the stimulation device.

In accordance with an embodiment of the present invention, the apparatus comprises implantable electrical components including at least one, or only one single voltage level guard and a capacitor or accumulator, wherein the charge and discharge of the capacitor or accumulator is controlled by use of the voltage level guard.

The source of energy may be external to the patient's body and the control device may control the source of energy to release wireless energy. The external source of energy may conveniently be incorporated in the hand-held wireless remote control. An additional source of energy may be implanted in the patient, wherein the implanted source of energy is activated by wireless energy released from the external source of energy, to supply energy, which is used in connection with the power of the stimulation device.

Alternatively, an energy storage device, preferably an electric accumulator, may be implanted in the patient for storing the wireless energy released from the external source of energy. The electric accumulator may comprise at least one capacitor or at least one rechargeable battery, or a combination of at least one capacitor and at least one rechargeable battery. Alternatively, a battery may be implanted in the patient for supplying electric energy to implanted electric energy consuming components of the apparatus, in addition to the supply of wireless energy. Where the control device comprises an implantable control unit the electronic circuit thereof and the stimulation device may be directly powered with transformed wireless energy, or energy from either the implanted energy storage device or battery.

The wireless energy may be directly used for the power of the stimulation device, i.e., the stimulation device is powered as the wireless energy is released from the external source of energy by the control device. In this case the term "directly" is used to mean, on one hand, that the stimulation device is promptly powered by using the released energy whiteout first storing the latter, and on the other hand, that the released energy may be somewhat delayed, in the order of seconds, by for instance an energy stabiliser before being used for the power of the stimulation device. As a result, a very simple control of the stimulation device is achieved and there are only a few implanted components of the apparatus. For example, there is no implanted source of energy, such as a battery, nor any implanted complicated signal control system. This gives the advantage that the apparatus will be extremely reliable.

In another embodiment of the present invention, the source of energy comprises an implantable internal source of energy. Thus, when the internal source of energy is implanted in a patient, the control device controls it from outside the patient's body to release energy. This solution is advantageous for sophisticated embodiments of the apparatus that have a relatively high consumption of energy that cannot be satisfied by the direct supply of wireless energy.

The internal source of energy preferably comprises an electric source of energy, such as an accumulator or a battery.

In yet another embodiment of the invention, the apparatus comprises a switch implanted in the patient for directly or indirectly switching the power of the stimulation device and an internal electric source of energy, such as a battery, implanted in the patient for supplying electric energy for the power of the stimulation device, wherein the switch directly or indirectly affects the supply of electric energy from the internal electric source of energy. This solution is advantageous for embodiments of the apparatus that have a relatively high consumption of energy that cannot be met by the direct supply of wireless energy.

The switch may switch between an off mode, in which the internal electric source of energy is not in use, and an on mode, in which the internal electric source of energy supplies electric energy for the power of the stimulation device. In this case, the switch is conveniently operated by the wireless energy released from the external source of energy to switch between the on and off modes. The control device, preferably the hand-held wireless remote control, may control the external source of energy to release the wireless energy. This gives the advantage that the lifetime of the implanted electric source of energy, such as a battery, can be significantly prolonged, since the implanted source of energy does not supply energy when the switch is in its off mode.

Alternatively, the wireless remote control controls the internal electric source of energy. In this case, the switch is operable by the wireless energy from the external source of energy to switch between an off mode, in which the internal electric source of energy and remote control are not in use, and a standby mode, in which the remote control is permitted to control the internal electric source of energy to supply electric energy for the power of the stimulation device.

In accordance with another alternative, the apparatus may include an energy transforming device to be implanted in the patient for transforming the wireless energy into storable energy, and an implantable energy storage device for storing the storable energy, wherein the switch is operable by energy from the implanted energy storage device to switch between an off mode, in which the internal electric source of energy is not in use, and an on mode, in which the internal electric source of energy supplies electric energy for the power of the stimulation device. In this alternative, the wireless remote control suitably controls the energy storage device to operate the switch.

An external data communicator may be provided outside the patient's body and an internal data communicator to be implanted in the patient may be provided for communicating with the external data communicator. The internal data communicator may feed data related to the patient, or related to the stimulation device, back to the external data communicator. Alternatively or in combination, the external data communicator may feed data to the internal data communicator. The internal data communicator may suitably feed data related to at least one physical signal of the patient.

Suitably, an implantable stabiliser, such as a capacitor, a rechargeable accumulator or the like, may be provided for stabilising the electric energy released by the control device. In addition, the control device may control the source of energy to release energy for a determined time period or in a determined number of energy pulses.

All of the above embodiments are preferably remote controlled by the hand-held wireless remote control. Thus, with the remote control it will be possible to adapt the function of the apparatus to the patient's need on a daily basis, which is beneficial with respect to the treatment of the patient. The wireless remote control may be capable of obtaining information on the condition of the stimulation device and of controlling the stimulation device in response to the information.

The remote control may transmit a carrier signal for carrying the control signal, wherein the carrier signal is frequency, amplitude or frequency and amplitude modulated, and is digital, analogue or digital and analogue. Also the control signal used with the carrier signal may be frequency, amplitude or frequency and amplitude modulated.

The control signal may comprise a wave signal, for example, a sound wave signal, such as an ultrasound wave signal, an electromagnetic wave signal, such as an infrared light signal, a visible light signal, an ultra violet light signal, a laser signal, a microwave signal, a radio wave signal, an x-ray radiation signal, or a gamma radiation signal. Where applicable, two or more of the above signals may be combined.

The control signal may be digital or analogue, and may comprise an electric or magnetic field. Suitably, the wireless remote control may transmit an electromagnetic carrier wave signal for carrying the digital or analogue control signal. For example, use of an analogue carrier wave signal carrying a digital control signal would give safe communication. The control signal may be transmitted in pulses by the wireless remote control.

The control device may be activated in a manual or non-manual manner to control the source of energy to release energy.

In the above-presented embodiments of the present invention, the released energy normally comprises electric energy, and an implantable capacitor having a capacity less than 0.1 µF may be provided for producing the above-mentioned train of energy pulses.

Generally, the wireless energy comprises a signal.

The apparatus may further comprise an implantable energy transforming device for transforming wireless energy, for example in the form of sound waves, directly or indirectly into electric energy, for the power of the stimulation device. More specifically, the energy transforming device may comprise a capacitor adapted to produce electric pulses from the transformed electric energy.

The stimulation device is advantageously embedded in a soft or gel-like material, such as a silicone material having a hardness less than 20 Shore.

The stimulation device suitably comprises a band for application around the urethral sphincter or bladder contraction muscle, wherein the band is provided with the electrodes for engaging the muscle. The electrodes may comprise hooks to secure the electrodes on the muscle.

All the above described various components may be combined in the different embodiments where applicable. Also the various functions described in connection with the above embodiments of the invention may be used in different applications, where applicable.

All the various ways of transferring energy and controlling the energy presented in the present specification may be practised by using all of the various components and solutions described.

In accordance with a third aspect of the invention, there is provided a method for treating a patient suffering from urinary incontinence, comprising implanting in the patient an electrically powered stimulation device in direct engagement with the urethral sphincter, electrically stimulating the urethral sphincter by the stimulation device to increase the tonus thereof, providing a hand-held wireless remote control adapted to control the stimulation device from outside the patient's body, and operating the wireless remote control by the patient holding it to:

i) switch off the electrically powered stimulation device, when the patient wants to urinate;

ii) switch on the electrically powered stimulation device, when the patient has finished urinating; and iii) control the stimulation device when various needs arise over the course of a day to promptly adjust the intensity of the electric stimulation of the urethral sphincter so that the tonus of the urethral sphincter is quickly increased.

Suitably, the patient operates the wireless remote control to control the stimulation device to temporarily increase the intensity of the electric stimulation of the urethral sphincter, so that the tonus of the urethral sphincter is increased, when the patient expects an abrupt increase in the abdominal pressure.

The method further comprises providing an external source of energy for transmitting wireless energy implanting in the patient an energy storage device, transmitting wireless energy from the external source of energy, loading the implanted energy storage device with the transmitted wireless energy, and controlling the implanted energy storage device to supply energy for operating the stimulation device.

In accordance with a fourth aspect of the present invention, there is provided a method for treating a patient suffering from urinary overflow incontinence, comprising implanting in the patient an electrically powered stimulation device in direct engagement with the urine bladder contraction muscle, providing a hand-held wireless remote control adapted to control the stimulation device from outside the patient's body, and operating the wireless remote control by the patient holding it to:

i) switch on the electrically powered stimulation device to electrically stimulate the urine bladder contraction muscle to contract the bladder, when the patient wants to urinate, and switch off the electrically powered stimulation device, when the patient has finished urinating; and ii) control the stimulation device when the patient is urinating to adjust the intensity of the electric stimulation of the urine bladder contraction muscle so that the bladder is emptied in a manner that is comfortable to the patient.

The method may further comprise providing an electrically powered additional stimulation device directly engaging the urethral sphincter, and electrically stimulating the urethral sphincter to increase the tonus thereof to counteract leakage of urine from the bladder. The patient may control the additional stimulation device using the hand-held wireless remote control to switch off the additional stimulation device, when the patient wants to urinate, and switch on the additional stimulation device, when the patient has finished urinating. The patient may also operate the wireless remote control to control the additional stimulation device to adjust the intensity of the electric stimulation of the urethral sphincter so that urine leakage from the bladder is satisfactorily counteracted.

BRIEF DESCRIPTION OF THE DRAWINGS

The invention is described in more detail in the following with reference to the accompanying drawings, in which.

Referring to the drawing figures, like reference numerals designate identical or corresponding elements throughout the several figures.

DETAILED DESCRIPTION OF THE INVENTION

Figure 1:
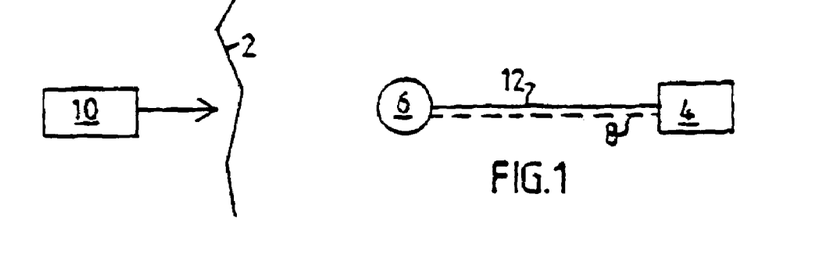
FIG. 1 is a schematic block diagram illustrating an embodiment of the urinary incontinence treatment apparatus of the invention, in which wireless energy is released from an external source of energy for use in the power of a stimulation device.

FIG. 1 schematically shows an embodiment of the urinary incontinence treatment apparatus of the invention having some parts implanted in a patient and other parts located outside the patient's body. Thus, in FIG. 1 all parts placed to the right of the patient's skin 2 are implanted and all parts placed to the left of the skin 2 are located outside the patient's body. The apparatus of FIG. 1 comprises an implanted electric stimulation device 4, which electrically engages the patient's urethral sphincter or urine bladder contraction muscle. An implanted control unit 6 controls the stimulation device 4 via a control line 8. An external control unit 10 includes an external source of energy and a wireless remote control transmitting a control signal generated by the external source of energy. The control signal is received by a signal receiver incorporated in the implanted control unit 6, whereby the control unit 6 controls the implanted stimulation device 4 in response to the control signal. The implanted control unit 6 also uses electric energy drawn from the control signal for powering the stimulation device 4 via a power supply line 12.

Figure 2:
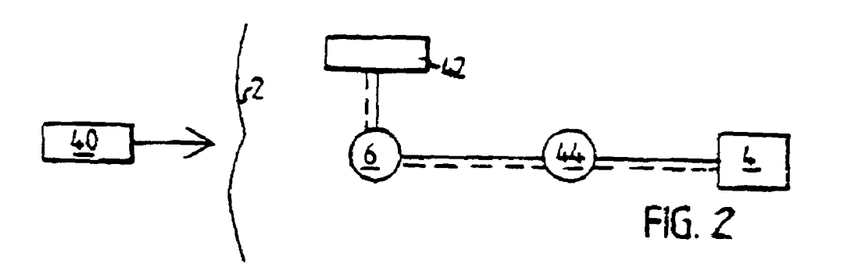
FIG. 2 is a schematic block diagram illustrating another embodiment of the invention, in which wireless energy is released from an internal source of energy.

FIG. 2 shows an embodiment of the invention identical to that of FIG. 1, except that an implanted internal electric source of energy in the form of a battery 42 is substituted for the external source of energy. Thus, an external control unit 40 without any source of energy is used in this embodiment. In response to a control signal from the external control unit 40 the implanted control unit 6 powers the stimulation device 4 with energy from the battery 42.

Figure 3:
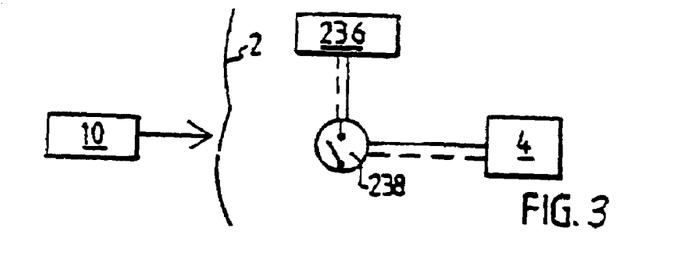
FIGS. 3 to 6 are schematic block diagrams illustrating four embodiments, respectively, of the invention, in which a switch is implanted in the patient for directly or indirectly switching the power of the stimulation device.

FIG. 3 shows an embodiment of the invention comprising the stimulation device 4, the external control unit 10, and an implanted source of energy 236 and an implanted switch 238. The switch 238 is operated by wireless energy released from the external source of energy of the external control unit 6 to switch between an off mode, in which the implanted source of energy 236 is not in use, and an on mode, in which the implanted source of energy 236 supplies energy for the power of the stimulation device 4.

Figure 4:
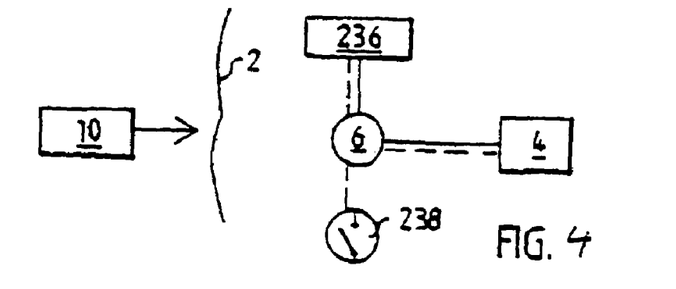

FIG. 4 shows an embodiment of the invention identical to that of FIG. 3, except that also the control unit 6 is implanted, in order to receive a control signal from the wireless remote control of the external control unit 10. The switch 238 is operated by the wireless energy from the external source of energy 10 to switch between an off mode, in which the implanted source of energy 236 and the wireless remote control of the external control unit 10 are not in use, i.e., the control unit 6 is not capable of receiving the control signal, and a standby mode, in which the wireless remote control is permitted to control the internal source of energy 236, via the implanted control unit 6, to supply energy for the power of the stimulation device 4.

Figure 5:
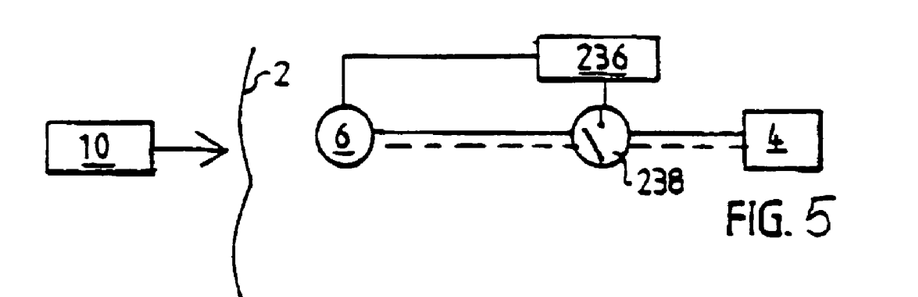

FIG. 5 shows an embodiment of the invention identical to that of FIG. 4, except that an energy transforming device for transforming the wireless energy into storable energy is incorporated in the implanted control unit 6 and that the implanted source of energy 236 is of a type that is capable of storing the storable energy. In this case, in response to a control signal from the external control unit 10, the implanted control unit 6 controls the switch 238 to switch from an off mode, in which the implanted source of energy 236 is not in use, to an on mode, in which the source of energy 36 supplies energy for the power of the stimulation device 4.

Figure 6:
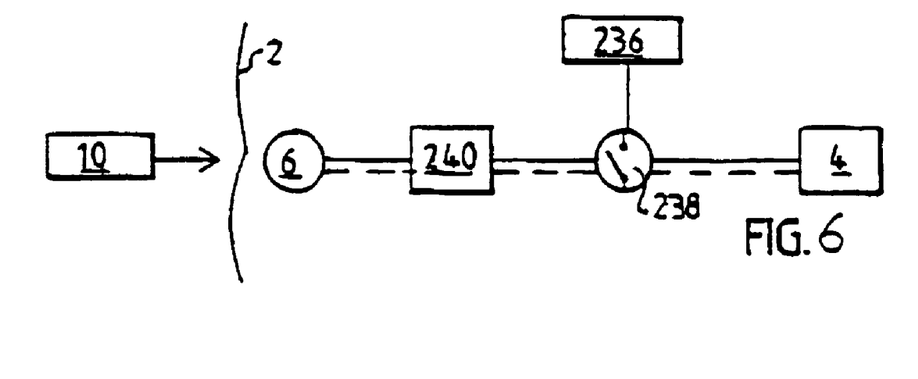

FIG. 6 shows an embodiment of the invention identical to that of FIG. 5, except that an energy storage device 240 also is implanted in the patient for storing the storable energy transformed from the wireless energy by the transforming device of the control unit 6. In this case, the implanted control unit 6 controls the energy storage device 240 to operate the switch 238 to switch between an off mode, in which the implanted source of energy 236 is not in use, and an on mode, in which the implanted source of energy 236 supplies energy for the power of the stimulation device 4.

Figure 7:
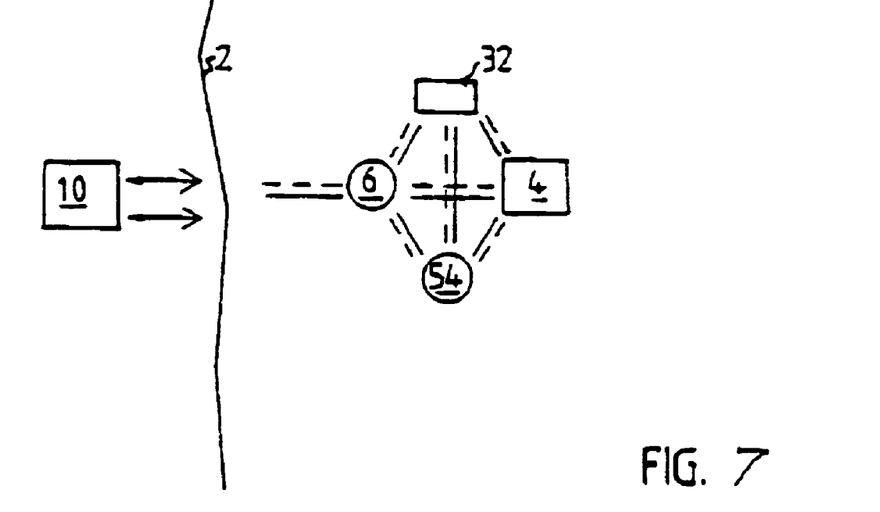
FIG. 7 is a schematic block diagram illustrating conceivable combinations of implantable components for achieving various communication options.

FIG. 7 schematically shows conceivable combinations of implanted components of the apparatus for achieving various communication possibilities. Basically, there are the implanted stimulation device 4, the implanted control unit 6 and the external control unit 10 including the external source of energy and the wireless remote control. As already described above the remote control transmits a control signal generated by the external source of energy, and the control signal is received by a signal receiver incorporated in the implanted control unit 6, whereby the control unit 6 controls the implanted stimulation device 4 in response to the control signal.

A sensor 54 may be implanted in the patient for sensing a physical parameter of the patient, such as the pressure in the urine bladder. The control unit 6, or alternatively the external control unit 10, may control the stimulation device 4 in response to signals from the sensor 54. A transceiver may be combined with the sensor 54 for sending information on the sensed physical parameter to the external control unit 10. The wireless remote control of the external control unit 10 may comprise a signal transmitter or transceiver and the implanted control unit 6 may comprise a signal receiver or transceiver. Alternatively, the wireless remote control of the external control unit 10 may comprise a signal receiver or transceiver and the implanted control unit 6 may comprise a signal transmitter or transceiver. The above transceivers, transmitters and receivers may be used for sending information or data related to the stimulation device from inside the patient's body to the outside thereof. For example, the battery 32 may be equipped with a transceiver for sending information on the charge condition of the battery.

Those skilled in the art will realise that the above various embodiments according to FIGS. 1-6 could be combined in many different ways.

Figure 8:
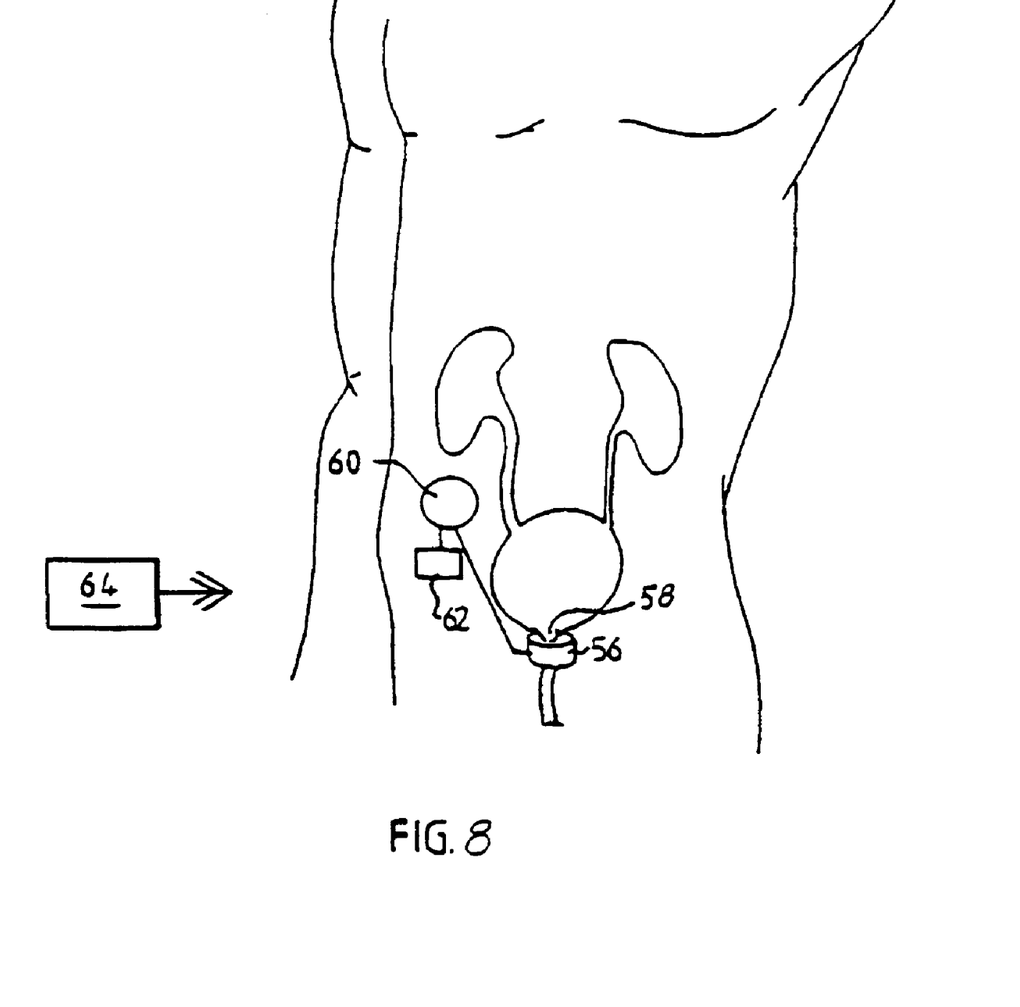
FIG. 8 illustrates the apparatus in accordance with the invention implanted in a patient.

FIG. 8 illustrates how any of the above-described embodiments of the urinary incontinence treatment apparatus of the invention may be implanted in a urinary stress or urge incontinent patient. Thus, an assembly of the apparatus implanted in the patient comprises a stimulation device in the form of a band 56, which is wrapped around the urethral sphincter 58. The band 58 is provided with electrodes that electrically engage the urethral sphincter. An implanted control unit 60 is provided for controlling the supply of electricity to the band 56. There is an implanted energy transforming device 62 for transforming wireless energy into electric energy. The transforming device 62 also includes a signal receiver. An external control unit 64 includes a signal transmitter for transmitting a control signal to the signal receiver of the implanted transforming device 62. The transforming device 62 is capable of transforming signal energy from the control signal into electric energy for powering the stimulation device 56 and for energising other energy consuming implanted components of the apparatus.

Figure 9:
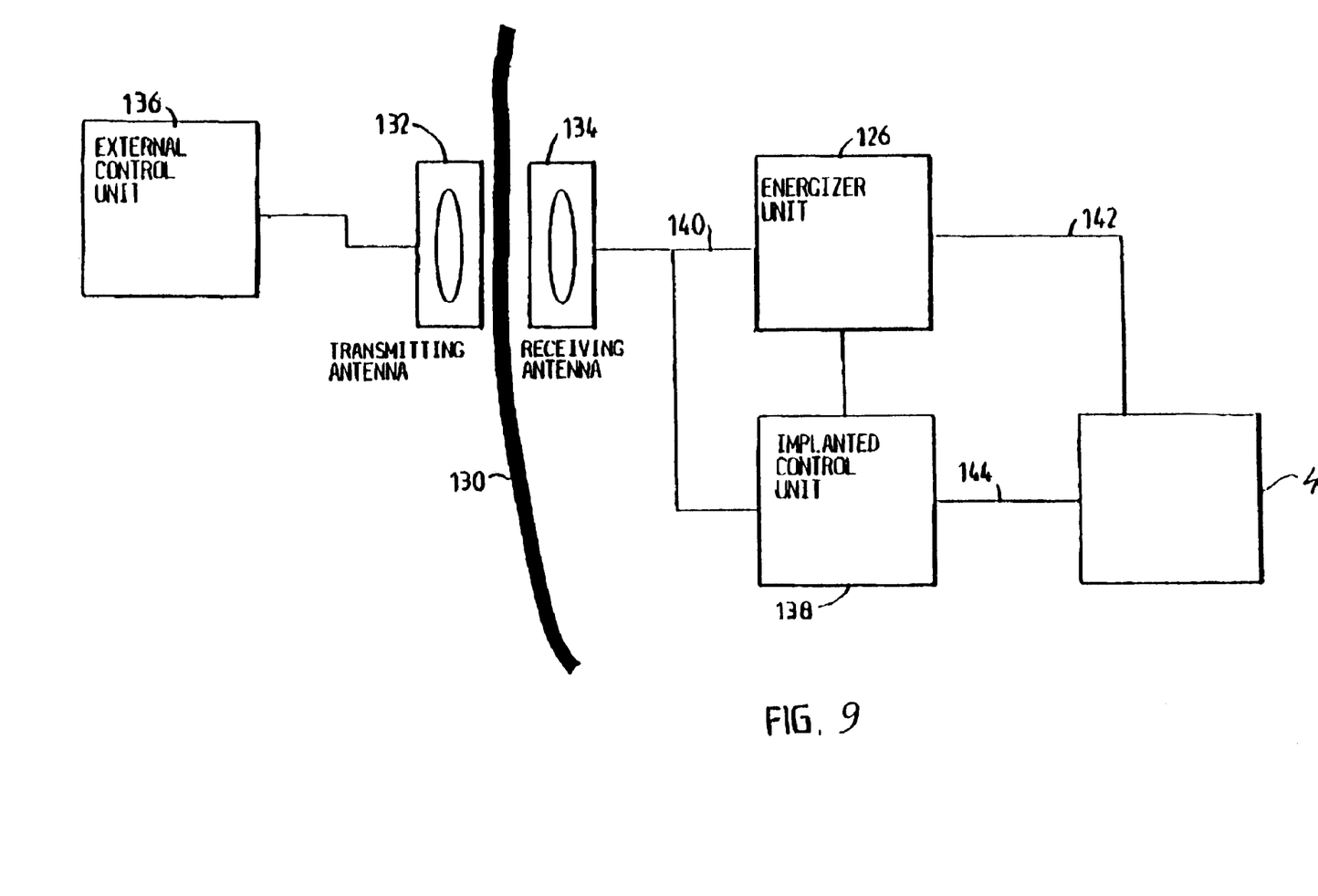
FIG. 9 is a block diagram illustrating remote control components of an embodiment of the invention.

FIG. 9 shows the basic parts of a wireless remote control of the apparatus of the invention including an implanted electric stimulation device 4. In this case, the remote control is based on the transmission of electromagnetic wave signals, often of high frequencies in the order of 100 kHz-1 gHz, through the skin 130 of the patient. In FIG. 9, all parts placed to the left of the skin 130 are located outside the patient's body and all parts placed to the right of the skin 130 are implanted. Any suitable remote control system may be used.

An external signal transmitting antenna 132 is to be positioned close to a signal receiving antenna 134 implanted close to the skin 130. As an alternative, the receiving antenna 134 may be placed for example inside the abdomen of the patient. The receiving antenna 134 comprises a coil, approximately 1-100 mm, preferably 25 mm in diameter, wound with a very thin wire and tuned with a capacitor to a specific high frequency. A small coil is chosen if it is to be implanted under the skin of the patient and a large coil is chosen if it is to be implanted in the abdomen of the patient. The transmitting antenna 132 comprises a coil having about the same size as the coil of the receiving antenna 134 but wound with a thick wire that can handle the larger currents that is necessary. The coil of the transmitting antenna 132 is tuned to the same specific high frequency as the coil of the receiving antenna 134.

An external control unit 136 comprises a microprocessor, a high frequency electromagnetic wave signal generator and a power amplifier. The microprocessor of the control unit 136 is adapted to switch the generator on/off and to modulate signals generated by the generator to send digital information via the power amplifier and the antennas 132, 134 to an implanted control unit 138. To avoid that accidental random high frequency fields trigger control commands, digital signal codes are used. A conventional keypad placed on the external control unit 136 is connected to the microprocessor thereof. The keypad is used to order the microprocessor to send digital signals to either power or not power the stimulation device. The microprocessor starts a command by applying a high frequency signal on the antenna 132. After a short time, when the signal has energised the implanted parts of the control system, commands are sent to power the stimulation device. The commands are sent as digital packets in the form illustrated below.

| Start pattern, | Command, | Count, | Checksum, |
| 8 bits | 8 bits | 8 bits | 8 bits |

The commands may be sent continuously during a rather long time period. When a new power or non-power step is desired the Count byte is increased by one to allow the implanted control unit 138 to decode and understand that another step is demanded by the external control unit 136. If any part of the digital packet is erroneous, its content is simply ignored.

Through a line 140, an implanted energiser unit 126 draws energy from the high frequency electromagnetic wave signals received by the receiving antenna 134. The energiser unit 126 stores the energy in a power supply, such as a large capacitor, powers the control unit 138 and powers the electric stimulation device 4 via a line 142.

The control unit 138 comprises a demodulator and a microprocessor. The demodulator demodulates digital signals sent from the external control unit 136. The microprocessor of the control unit 138 receives the digital packet, decodes it and, provided that the power supply of the energiser unit 126 has sufficient energy stored, powers the stimulation device 4 via a line 144.

Alternatively, the energy stored in the power supply of the energiser unit may only be used for powering a switch, and the energy for powering the stimulation device 4 may be obtained from another implanted power source of relatively high capacity, for example a battery. In this case the switch is adapted to connect said battery to the control unit 138 in an on mode when the switch is powered by the power supply and to keep the battery disconnected from the control unit in a standby mode when the switch is not powered.

Although the present invention has been described in terms of particular embodiments and methods, it is not intended that the invention be limited to those embodiments and methods. Modifications of the embodiments and methods within the spirit of the invention will be apparent to those skilled in the art. The scope of the invention is defined by the claims that follow.

What is claimed is:

1. An apparatus for treating urinary incontinence, comprising an electrically powered stimulation device implantable in a urinary incontinent patient and adapted to electrically stimulate the patient's natural urethral sphincter all the time, except when the patient wants to urinate, to maintain a sufficient tonus of the patient's natural urethral sphincter that prevents urine from passing past the patient's natural urethral sphincter, and a control device that controls said stimulation device, said control device including a hand-held wireless remote control that generates a control signal to control said stimulation device from outside the patient's body to:

i) switch off said electrically powered stimulation device, when the patient wants to urinate, and switch on said electrically powered stimulation device, when the patient has finished urinating; and ii) control said stimulation device as needed at any time over the course of a day to promptly adjust the intensity of the electric stimulation of the patient's natural urethral sphincter, so that the tonus of the patient's natural urethral sphincter is instantly increased, whereby the patient is able to maintain continence.

2. An apparatus according to claim 1, wherein said wireless remote control is adapted to be operated to control said stimulation device to temporarily increase the intensity of the electric stimulation of the urethral sphincter, so that the tonus of the urethral sphincter is increased, when the patient expects an abrupt increase in the abdominal pressure.

3. An apparatus according to claim 1, wherein said wireless remote control is adapted to be operated to control said stimulation device to adjust the intensity of the electric stimulation of the urethral sphincter to one of a plurality of different preselected intensity levels.

4. An apparatus according to claim 1, further comprising a source of energy, wherein said control device also controls said source of energy to supply energy for operating said stimulation device.

5. An apparatus according to claim 4, wherein said source of energy comprises an electric source of energy and said control device is adapted to control said electric source of energy to supply said stimulation device with electric energy.

6. An apparatus according to claim 5, wherein said stimulation device comprises electrodes adapted to engage with the urethral sphincter, said electric source of energy is adapted to provide a current through said electrodes, and said control device is adapted to control said electric source of energy to release electric energy such that the intensity of the current through said electrodes amounts to a predetermined value.

7. An apparatus according to claim 6, wherein said control device is adapted to control said electric source of energy to release electric energy in the form of an alternating current.

8. An apparatus according to claim 5, wherein said control device is adapted to control said electric source of energy to continuously supply said stimulation device with electric energy to keep the urethral sphincter closed, except when the patient operates said wireless remote control to stop the stimulation of the urethral sphincter.

9. An apparatus according to claim 4, wherein said source of energy is intended to be external to the patient's body when said stimulation device is implanted therein, and said control device is adapted to control the external source of energy to supply wireless energy.

10. An apparatus according to claim 9, further comprising an energy storage device implantable in the patient for storing said wireless energy supplied by said external source of energy.

11. An apparatus according to claim 10, wherein said energy storage device comprises an accumulator.

12. An apparatus according to claim 11, wherein said accumulator comprises an electric accumulator.

13. An apparatus according to claim 12, wherein said electric accumulator comprises at least one capacitor or at least one rechargeable battery, or a combination of at least one capacitor and at least one rechargeable battery.

14. An apparatus according to claim 9, wherein said control device is adapted to control said external source of energy to supply wireless energy for direct use in connection with the operation of said stimulation device.

15. An apparatus according to claim 14, further comprising an activatable source of energy implantable in the patient, wherein said implantable source of energy is activated by wireless energy supplied by said external source of energy, to supply energy which is used in connection with the operation of said stimulation device.

16. An apparatus according to claim 14, wherein said control device is adapted to control said external source of energy to intermittently supply wireless energy in the form of a train of energy pulses for direct use in connection with the operation of said stimulation device.

17. An apparatus according to claim 16, wherein said control device is adapted to control said source of energy to release electric energy, and further comprising an implantable capacitor for producing said train of energy pulses from the released energy.

18. An apparatus according to claim 17, wherein said capacitor has a capacity less than 0.1 µF.

19. An apparatus according to claim 9, further comprising an implantable stabiliser for stabilising said energy supplied by said external source of energy.

20. An apparatus according to claim 19, wherein said energy supplied by said external source of energy comprises electric energy and said stabiliser comprises at least one capacitor.

21. An apparatus according to claim 9, wherein said wireless energy comprises said control signal.

22. An apparatus according to claim 9, further comprising an implantable energy transforming device for transforming said wireless energy directly or indirectly into electric energy for operating said stimulation device, as said energy transforming device transforms said wireless energy.

23. An apparatus according to claim 22, wherein said energy transforming device comprises a capacitor.

24. An apparatus according to claim 23, wherein said capacitor is adapted to produce electric pulses from said transformed electric energy.

25. An apparatus according to claim 9, further comprising an implantable energy transforming device for transforming said wireless energy in the form of sound waves into kinetic energy.

26. An apparatus according to claim 9, further comprising an implantable energy transforming device for transforming said wireless energy in the form of sound waves directly or indirectly into electric energy.

27. An apparatus according to claim 4, wherein said source of energy comprises an implantable internal source of energy.

28. An apparatus according to claim 27, wherein said internal source of energy comprises an electric source of energy.

29. An apparatus according to claim 28, wherein said internal electric source of energy comprises at least one accumulator, at least one capacitor or at least one rechargeable battery, or a combination of at least one capacitor and at least one rechargeable battery.

30. An apparatus according to claim 4, further comprising a switch implantable in the patient for directly or indirectly switching the operation of said stimulation device.

31. An apparatus according to claim 30, wherein said source of energy comprises an internal electric source of energy implantable in the patient for supplying electric energy to said stimulation device, wherein said switch directly or indirectly affects the supply of electric energy from said internal electric source of energy.

32. An apparatus according to claim 31, wherein said wireless remote control controls said internal electric source of energy.

33. An apparatus according to claim 31, wherein said source of energy further comprises an external source of energy and said control device is adapted to control said external source of energy to supply wireless energy, and further comprising an energy transforming device implantable in the patient for transforming said wireless energy into storable energy and an energy storage device implantable in the patient for storing said storable energy.

34. An apparatus according to claim 33, wherein said switch is adapted to be operated by energy from said implantable energy storage device to switch between an "off" mode, in which said internal electric source of energy is not in use, and an "on" mode, in which said internal electric source of energy supplies electric energy to said stimulation device.

35. An apparatus according to claim 34, wherein said control device controls said energy storage device to operate said switch.

36. An apparatus according to claim 31, wherein said source of energy further comprises an external source of energy and said control device is adapted to control said external source of energy to supply wireless energy, the apparatus further comprising an energy transforming device implantable in the patient for transforming said wireless energy into electric energy, which is stored by said internal electric source of energy.

37. An apparatus according to claim 36, wherein said switch switches from an "off" mode, in which said internal electric source of energy is not in use, to an "on" mode, in which said internal source of electric energy supplies energy to said stimulation device.

38. An apparatus according to claim 37, wherein said control device controls said switch to switch between said "on" and "off" modes.

39. An apparatus according to claim 4, wherein said control device controls said source of energy to supply energy for a determined time period.

40. An apparatus according to claim 4, wherein said control device controls said source of energy to supply energy in a determined number of energy pulses.

41. An apparatus according to claim 4, wherein said control device is adapted to control said source of energy to supply energy in a non-invasive manner.

42. An apparatus according to claim 1, wherein said control device is adapted to control said stimulation device to vary the intensity of the electric stimulation of the urethral sphincter over time.

43. An apparatus according to claim 1, wherein said remote control is adapted to be operated to control said stimulation device to increase the intensity of the electric stimulation of the urethral sphincter so that the tonus of the urethral sphincter is increased, when the patient feels need but does not want to urinate.

44. An apparatus according to claim 1, further comprising at least one implantable sensor for sensing at least one physical parameter of the patient, wherein said control device controls said stimulation device in response to said sensor.

45. An apparatus according to claim 44, wherein said sensor is adapted to sense as the physical parameter the pressure against the urethral sphincter exerted by the urine bladder.

46. An apparatus according to claim 45, wherein said control device is adapted to control said electric stimulation device to increase the stimulation on the urethral sphincter in response to said sensor sensing an abrupt increase in pressure caused by bladder contraction or increased abdominal pressure.

47. An apparatus according to claim 44, wherein said sensor is adapted to sense as the physical parameter the patient's orientation.

48. An apparatus according to claim 47, wherein said control device is adapted to control said electric stimulation device to decrease the stimulation intensity on the urethral sphincter in response to said sensor sensing that the patient is lying down.

49. An apparatus according to claim 44, wherein said sensor comprises a pressure sensor for directly or indirectly sensing as the physical parameter the pressure in the urine bladder.

50. An apparatus according to claim 44, wherein said control device comprises an external control unit outside the patient's body, said external control unit controlling said stimulation device in response to signals from said sensor.

51. An apparatus according to claim 44, wherein said control device comprises an internal control unit implantable in the patient, said internal control unit controlling said stimulation device in response to signals from said sensor.

52. An apparatus according to claim 51, wherein said external control unit stores information on said physical parameter sensed by said sensor and is manually operated to control said stimulation device based on said stored information.

53. An apparatus according to claim 44, further comprising at least one implantable sender for sending information on said physical parameter sensed by said sensor.

54. An apparatus according to claim 1, wherein said stimulation device comprises electrodes adapted to engage with the urethral sphincter, and a band for application around the urethral sphincter and provided with said electrodes.

55. An apparatus according to claim 1, wherein said stimulation device comprises electrodes provided with hooks adapted to be inserted into the urethral sphincter.

56. An apparatus according to claim 1, wherein said control device comprises an internal control unit implantable in the patient for controlling said stimulation device.

57. An apparatus according to claim 56, wherein said internal control unit is programmable.

58. An apparatus according to claim 57, wherein said control device comprises an external control unit intended to be outside the patient's body, said internal control unit being programmable by said external control unit.

59. An apparatus according to claim 58, wherein said external control unit controls said internal control unit in accordance with a doctor mode only authorised for a doctor.

60. An apparatus according to claim 58, wherein said external control unit controls said internal control unit in accordance with a patient mode permitted for the patient.

61. An apparatus according to claim 57, wherein said internal control unit is programmable for controlling said stimulation device over time.

62. An apparatus according to claim 61, wherein said internal control unit comprises a microprocessor.

63. An apparatus according to claim 1, further comprising an external data communicator intended to be outside the patient's body, an internal data communicator implantable in the patient for communicating with said external communicator, and means for generating data related to the patient, wherein said internal data communicator feeds said data related to the patient back to said external data communicator.

64. An apparatus according to claim 63, wherein said means generates data related to at least one physical signal of the patient.

65. An apparatus according to claim 1, further comprising an external data communicator intended to be outside the patient's body, an internal data communicator implantable in the patient for communicating with said external communicator, and means for generating data related to said stimulation device, wherein said internal data communicator feeds said data related to said stimulation device.

66. An apparatus according to claim 1, further comprising information generating means for generating information on the condition of said stimulation device when said stimulation device is implanted, wherein said remote control is capable of obtaining said generated information and of controlling said stimulation device in response to said information.

67. An apparatus according to claim 1, wherein said wireless remote control comprises at least one external signal transmitter or transceiver and at least one internal signal receiver or transceiver implantable in the patient.

68. An apparatus according to claim 1, wherein said wireless remote control comprises at least one external signal receiver or transceiver and at least one internal signal transmitter or transceiver implantable in the patient.

69. An apparatus according to claim 1, wherein the control device controls the stimulation device by means of a control signal, and wherein said remote control transmits a carrier signal for carrying said control signal.

70. An apparatus according to claim 69, wherein said carrier signal is frequency, amplitude or frequency and amplitude modulated.

71. An apparatus according to claim 69, wherein said carrier signal is digital, analogue or digital and analogue.

72. An apparatus according to claim 69, wherein said control signal used with said carrier signal is frequency, amplitude or frequency and amplitude modulated.

73. An apparatus according to claim 1, wherein the control device controls the stimulation device by means of a control signal, and wherein said control signal comprises a wave signal comprising one of a sound wave signal including an ultrasound wave signal, an electromagnetic wave signal including an infrared light signal, a visible light signal, an ultra violet light signal and a laser light signal, a micro wave signal, a radio wave signal, an x-ray radiation signal, and a gamma radiation signal.

74. An apparatus according to claim 1, wherein the control device controls the stimulation device by means of a control signal, and wherein said control signal comprises an electric, magnetic or electric and magnetic field.

75. An apparatus according to 1, wherein the control device controls the stimulation device by means of a control signal, and wherein said control signal is digital, analogue or digital and analogue.

76. An apparatus according to claim 75, wherein said remote control transmits an electromagnetic carrier wave signal for carrying the digital or analogue control signal.

77. An apparatus according to claim 1, wherein the control device controls the stimulation device by means of a control signal, and wherein said control signal is transmitted in pulses by said wireless remote control.

78. An apparatus according to claim 1, wherein said stimulation device is embedded in a soft material.

79. An apparatus according to claim 1, wherein said stimulation device is embedded in a silicone material having hardness less than 20 Shore.

80. An apparatus according to claim 1, wherein said control device controls said stimulation device to cyclically alternate between an operation mode, in which the urethral sphincter is stimulated, and a rest mode, in which the urethral sphincter is not stimulated.

81. An apparatus according to claim 80, wherein the urethral sphincter is stimulated with energy pulses when the stimulation device is in an operation mode.

82. A method for treating a patient suffering from urinary incontinence, comprising:
  implanting in the patient an electrically powered stimulation device in direct engagement with the urethral sphincter,
  electrically stimulating the urethral sphincter by the stimulation device to increase the tonus thereof,
  providing a hand-held wireless remote control adapted to control the stimulation device from outside the patient's body, and
  operating the wireless remote control by the patient holding it to:
    i) switch off the electrically powered stimulation device, when the patient wants to urinate;
    ii) switch on the electrically powered stimulation device, when the patient has finished urinating; and
    iii) control the stimulation device when various needs arise over the course of a day to promptly adjust the intensity of the electric stimulation of the urethral sphincter so that the tonus of the urethral sphincter is instantly increased.

83. A method according to claim 82, wherein the patient operates the wireless remote control to control the stimulation device to temporarily increase the intensity of the electric stimulation of the urethral sphincter, so that the tonus of the urethral sphincter is increased, when the patient expects an abrupt increase in the abdominal pressure.

84. A method according to claim 82, further comprising:
  providing an external source of energy for transmitting wireless energy,
  implanting in the patient an energy storage device,
  transmitting wireless energy from the external source of energy,
  loading the implanted energy storage device with the transmitted wireless energy, and
  controlling the implanted energy storage device to supply energy for operating the stimulation device.

* * * * *